Figure 3:
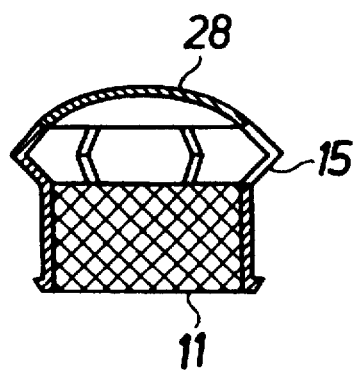

United States Patent [19]
Persson

[11] Patent Number: 5,738,095
[45] Date of Patent: Apr. 14, 1998

[54] TRACHEOSTOMA DEVICE

[75] Inventor: Jan-Ove Persson, Hoor, Sweden

[73] Assignee: Atos Medical AB, Horby, Sweden

[21] Appl. No.: 668,733

[22] Filed: Jun. 24, 1996

Related U.S. Application Data

[63] Continuation-in-part of PCT/SE94/01229, Dec. 21, 1994.

[30] Foreign Application Priority Data

Dec. 23, 1993 [SE] Sweden ................. 9304273

[51] Int. Cl.⁶ ........................................ A61M 16/00
[52] U.S. Cl. .................. 128/207.14; 128/207.16; 128/911; 128/912; 128/DIG. 26; 128/201.13; 623/9
[58] Field of Search .............. 128/200.26, 201.13, 128/207.16, 207.14, 207.29, 911, 912, DIG. 26; 623/9

[56] References Cited

U.S. PATENT DOCUMENTS

| | | | |
|---|---|---|---|
| 2,804,076 | 8/1957 | Giraudon | 128/207.16 |
| 4,040,428 | 8/1977 | Clifford | 128/207.16 |
| 4,060,856 | 12/1977 | Edwards | 623/9 |
| 4,223,411 | 9/1980 | Schoendorfer et al. | 128/207.16 |
| 4,325,366 | 4/1982 | Tabor . | |
| 4,538,607 | 9/1985 | Saul | 128/207.16 |
| 4,582,058 | 4/1986 | Depel et al. . | |
| 4,971,054 | 11/1990 | Andersson et al. . | |
| 5,059,208 | 10/1991 | Coe et al. . | |
| 5,064,433 | 11/1991 | Blom et al. . | |
| 5,107,828 | 4/1992 | Kross et al. | 128/207.14 |
| 5,123,922 | 6/1992 | Berg | 128/207.16 |
| 5,259,378 | 11/1993 | Huchon et al. . | |
| 5,391,205 | 2/1995 | Knight . | |
| 5,487,382 | 1/1996 | Bezicot | 128/207.14 |

FOREIGN PATENT DOCUMENTS

| | | |
|---|---|---|
| 0 078 685 | 5/1983 | European Pat. Off. . |
| WO 96/08860 | 5/1993 | European Pat. Off. . |
| 3436777 | 4/1985 | Germany . |
| 463649 | 1/1991 | Sweden . |
| 466990 | 5/1992 | Sweden . |
| 467195 | 6/1992 | Sweden . |
| 467289 | 6/1992 | Sweden . |
| 930617 | 6/1993 | Sweden . |

*Primary Examiner*—Vincent Millin
*Assistant Examiner*—William J. Deane, Jr.
*Attorney, Agent, or Firm*—Merchant, Gould, Smith, Edell, Welter, & Schmidt, P.A.

[57] ABSTRACT

Device to be connected to a tracheostoma, comprising a filter housing (10) for receiving a moisture and heat exchanging filter (11) said filter housing having a first opening (12) to be connected to the patient's stoma and at least one second opening (14) at the opposite side of the filter (11).

According to the invention there is provided at said second opening (14) of the filter housing (10) a valve member for closing said second opening, said valve member being spring biased to an open position and being adapted to be manually closed by means of a finger against the spring bias.

8 Claims, 2 Drawing Sheets

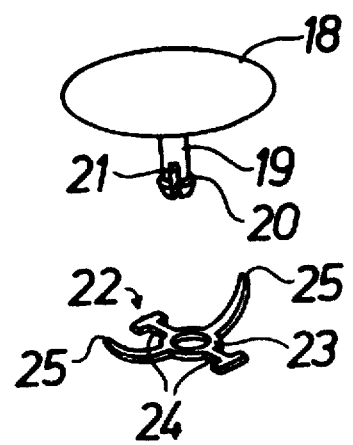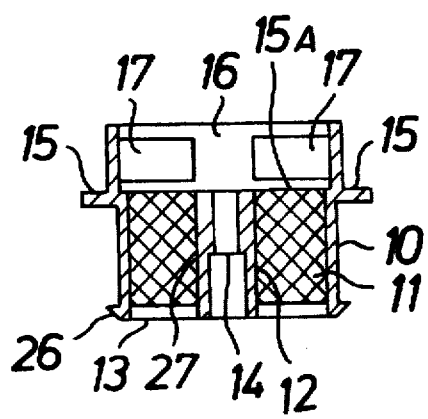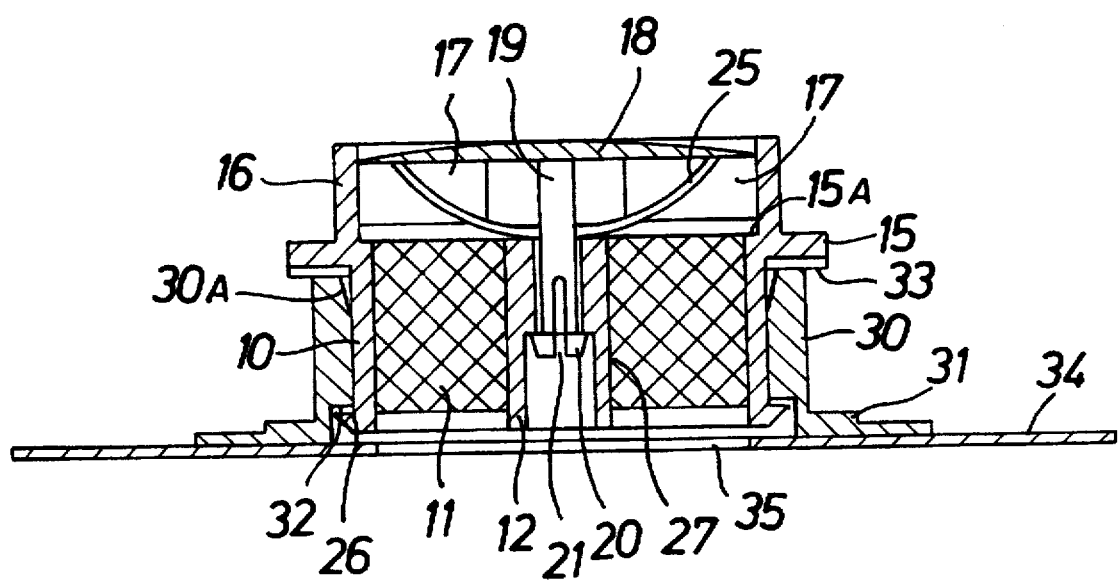

TRACHEOSTOMA DEVICE

The present application is a continuation in part of the International application No. PCT/SE94/01229 filed Dec. 21, 1994.

The invention relates to a device to be connected to a tracheostoma.

Due to disease it is sometimes necessary to remove by surgery the larynx (laryngectomy). In order that breathing will still be possible a so called tracheostoma must be opened at the outside of the throat.

In connection with laryngectomy also the ability to talk is lost because the vocal cords must be excised at the surgery, and in order to restore to some extent the ability to talk it is possible to open by surgery a fistula between esophagus and trachea for the passage of air to the oral cavity. In the fistula a so called voice prosthesis is fixed, and provided that the tracheostoma is blocked the patient can force air through the voice prosthesis and thus induce vibrations in the upper portion of the esophagus and in that way produce acceptable talk.

Voice prostheses of this type are disclosed i.a. in SE-B-463 649, SE-A-8904365-7, U.S. Pat. No. 4,614,516 and U.S. Pat. No. 5,064,433. It is necessary when using these prostheses that the patient in some way covers the tracheostoma for example by one or more fingers. However, this causes some inconvenience to the patient i.a. due to the fact that the stoma often is coated by secretion and can have an irregular shape and thus is difficult to cover. After laryngectomy the generation of secretion moreover increases, and further symptoms of irritation may arise due to the function of the nose being lost. Another serious drawback is that the patient is troubled by the appearance of the stoma and wishes to conceal it.

Another way of blocking the stoma is to use stoma valves wherein an accelerating flow of air initiates closing of the valve. Embodiments of such valves are disclosed i.a. in U.S. Pat. No. 5,059,208, U.S. Pat. No. 4,582,058 and U.S. Pat. No. 4,325,366. The drawback of these valves is that the high pressure which is sometimes necessary for talking, forces the valve to come loose from the throat. It is also difficult for some patients to generate the air shock necessary in order to close the valve. These valves moreover often are not very attractive aesthetically due to the dimensions thereof which make it difficult to conceal the valves under garments.

By laryngectomy the patient looses the moisture and heat exchanging function as well as the filtering function obtained when the breathing air passes through the oral and nasal cavities with the result that the inhalation air often is felt to be too dry, cold and entrained by particles. In SE-B-466 990, SE-B-467 125 and SE-B-467 289 there are disclosed so called breathing protections having a filter which absorbs the moisture and heat of the exhalation air. In order to make possible some kind of talk these devices must be covered by the fingers the drawback of secretion thus still remaining.

The purpose of the invention is to overcome the drawbacks and shortcomings mentioned above of prior art devices used in tracheostomas and to provide a manually controlled device having filter and valve function as well as moisture and heat exchanging function.

For the purpose mentioned above the invention provides a stoma device comprising a filter housing having a first opening at one end thereof to be connected to the tracheostoma, and at least one second opening at the opposite end of the filter housing; a moisture and heat exchanging filter mounted in said filter housing between said first and second openings; a valve member at said second opening of the filter housing; and means resiliently biasing said valve member to an open position, said valve member being adapted to be manually actuated against said bias for closing said second opening.

Figure 4:
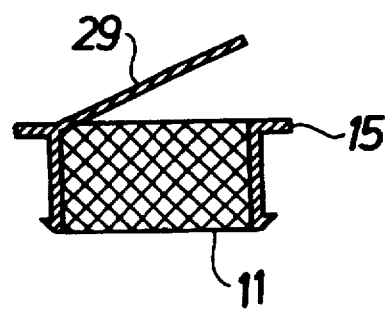
Figure 5:
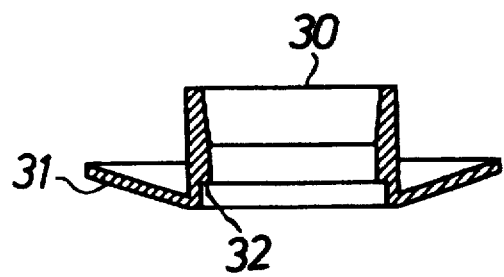
Figure 6:
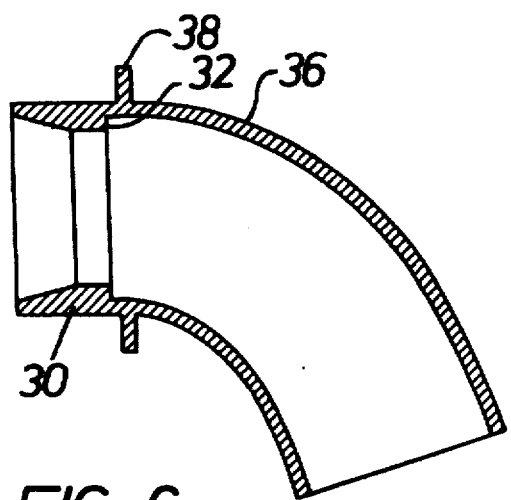

The invention will be explained in more detail by illustrative embodiments reference being made to the accompanying drawings in which FIG. 1 is an exploded view of a device according to the invention, partly in perspective view and partly in axial cross-sectional view, FIG. 2 is an enlarged axial cross-sectional view of the device according to the invention mounted in a holder, FIG. 3 is an axial cross-sectional view of an alternative embodiment of the device according to the invention, FIG. 4 is an axial cross-sectional view of a further alternative embodiment of the device according to the invention, FIG. 5 is an axial cross-sectional view of a modified holder for the device according to the invention, and FIG. 6 is an axial cross-sectional view of another modified holder for the device according to the invention.

The device according to the invention as shown in FIGS. 1 and 2 comprises a cylindrical filter housing 10 in which an annular moisture and heat exchanging filter 11 is received. The filter housing 10 forms a central tube 12 supported by radial arms 13 at one end of the housing said arms forming a stop element for the filter 11. The tube 12 forms an inside shoulder 14 between narrower and wider portions of the passage formed by the tube 12. At the other end of the filter housing 10 a radially projecting outside annular flange 15 and an inner shoulder 15A are provided. A rim 16 forms an axial extension of the filter housing 10 between the flange 15 and the shoulder 15A. Apertures 17 for breathing air are provided in the rim 16.

A valve member comprises a lid 18 having a central pin 19 which at one end thereof forms a bead 20 having an outside diameter which is larger than the inside diameter of the narrower portion of the passage formed by the tube 12, and forms a slot 21. A spring 22 shaped as a cross has a central annular portion 23. One pair of radially opposite arms 24 of the cross are plane while the other pair of radially opposite arms 25 are curved.

The device according to the invention is intended to be a one-way product which easily can be replaced at low cost after having been used for a predetermined period. The material of the device therefore suitably is a plastic material. For example, the filter housing 10 and the lid 18 as well as the pin 19 can be made of polypropylene or polyethylene. The spring preferably is made of acetaldehyde resin, for example DELRIN, while the filter preferably consists of foamed polyurethane impregnated with litium chloride or potassium chloride in order to increase the moisture and heat exchanging ability of the filter.

The filter 11 is located in the filter housing 10 and engages the radial arms 13, the tube 12 being received in a central passage 27 of the annular filter which thus encircles the tube 12. The spring 22 is located on the filter so that the arms 24 engage the filter and the arms 25 extend upwards away from the filter. The pin 19 of the lid 18 is received in the central annular portion 23 of the spring and is inserted into of the passage formed by the tube 12, the bead 20 being resiliently compressed under closure of the slot 21 when passing through the narrower portion of the passage. When the bead 20 then passes into the wider portion of the passage the bead will snap outwards at the shoulder 14. The bead 20 then retains the pin 19 in the tube 12 with the lid 18 spaced from the filter by the spring 22 but the pin can be axially displaced in the tube when the lid 18 is pressed towards the filter against the resilient bias provided by the spring 22.

The device shall be mounted with the end of the housing 10, where the arms 13 are provided, in register with a tracheostoma of a patient, and for mounting the device a holder is provided which with reference to FIG. 2 comprises a cylindrical stud 30 having a flange 31 at one end thereof. This holder should be made of a soft plastic material, and the device is mounted therein by being pushed into the hollow stud 30 with the outside bead 26 forming the leading end of the device the insertion being facilitated by a bevelled surface 30A in the hollow stud 30. The bead has an outside diameter which is larger than the inside diameter of the hollow stud 30 so that the stud will yield elastically when the bead 26 passes therethrough. The hollow stud 30 forms a shoulder 32 and the bead 26 will engage this shoulder in order to maintain the device in the holder with spacers 33 on the flange 15 engaging the opposite end of the hollow stud 30. The bead 26 is bevelled in order to facilitate the insertion of the device into the holder. The device can be removed from the holder by pulling the device outwards from the holder the bead 26 disengaging the shoulder 32 under resilient yielding of the hollow stud. The flange 31 is glued or in another suitable way attached to an annular sheet 34 of textile or plastic material which forms a central opening 35 in register with the adjacent opening of the housing 10. On the side opposite to the flange 31 the sheet 34 has a pressure sensitive adhesive so that the holder can be removably attached to the throat of the patient.

In order to generate talk the lid 18 is exposed to a light pressure from a finger until the lid closes off the outer end of the housing 10 by sealingly engaging the shoulder 15A. The device can be closed in this manner even if it is covered by garments. At the same time the device is prevented from coming loose from the stoma because it is pressed against the throat by the finger during talking. The spring 22 due to the shape thereof holds the filter 11 in position and also acts as a return spring so that the lid 18 after the pressure having been relieved will return to the starting position thereof. The rim 16 reduces the risk of the valve member being inadvertently closed for some reason or other, and since the starting position of the lid 18 is spaced from the filter 11 breathing air can pass through the apertures 17 when the device is open, i.e. when the lid 18 is in the outer non-actuated position thereof shown in FIG. 2.

In FIGS. 3 and 4 two alternative embodiments of the device of the invention are shown. The valve member in FIG. 3 comprises a spring element 28 of an elastic material, which collapses and seals when pressed down towards the filter, for example by means of a finger. Alternatively the valve member can comprise a flap 29, FIG. 4, which can be pressed resiliently towards the filter.

In FIGS. 5 and 6 there are shown alternative embodiments of the holder of the device according to the invention. The holder in FIG. 5 comprises a hollow stud 30 with an inside shoulder 32, an outside projecting annular flange 31 being provided at one end of said stud. After application to the tracheostoma the flange 31 shall engage the outside of the throat and be attached by means of adhesive tape. The device of the invention is then inserted into the holder and is retained therein by the outside bead 26 engaging the shoulder 32. Alternatively, there may be provided in the outside of the housing 10 a groove for engagement with a bead in the holder. The holder of FIG. 6 is intended to be applied to the tracheostoma on the inside of the trachea and comprises a tubular piece 36 having an inside shoulder 37 and an outside projecting annular flange 38 spaced from one end. This flange 38 is intended to engage the outside of the throat and can be attached by means of tape.

I claim:

1. Device to be connected to a tracheostoma, comprising a filter housing having a first opening at one end thereof to be connected to the tracheostoma, and at least one second opening at the opposite end of the filter housing; a moisture and heat exchanging filter mounted in said filter housing between said first and second openings; a valve member at said second opening of the filter housing; and means resiliently biasing said valve member to an open position, said valve member being adapted to be manually actuated against said bias for closing said second opening.

2. Device according to claim 1, further comprising a rim at said second opening of the filter housing to prevent unintended closing of the valve member.

3. Device according to claim 1, wherein the valve member comprises a lid having a central pin, and a spring between the lid and said filter.

4. Device according to claim 3, wherein said spring is cross-shaped forming at least one pair of radially opposite arms in one plane, which engage said filter, and at least one pair of radially opposite curved arms which are directed away from the filter towards the lid.

5. Device according to claim 4, wherein said filter housing, the lid, and the pin are made of a plastic material in the group comprising polyethylene and polypropylene.

6. Device according to claim 3, wherein the spring is made of acetaldehyde resin.

7. Device according to claim 1, wherein the filter is made of foamed polyurethane.

8. Device according to claim 7, wherein the filter is impregnated with a material in the group comprising lithium chloride and potassium chloride.

* * * * *